United States Patent [19]

Kojima

[11] Patent Number: 4,959,063
[45] Date of Patent: Sep. 25, 1990

[54] SPINAL NEEDLE WITH OPTICAL FIBER MEANS FOR RADIATING A LASER BEAM

[75] Inventor: Toshio Kojima, Tokyo, Japan

[73] Assignee: OSADA Research Institute, Ltd., Tokyo, Japan

[21] Appl. No.: 244,437

[22] Filed: Sep. 14, 1988

[30] Foreign Application Priority Data

May 12, 1988 [JP] Japan .................................. 63-63175

[51] Int. Cl.$^5$ .......................................... A61B 17/36
[52] U.S. Cl. .......................................... 606/15; 604/44
[58] Field of Search .................... 128/303.1, 6; 604/21, 604/44, 51, 161, 164, 170, 171, 267; 606/3, 14–16

[56] References Cited

U.S. PATENT DOCUMENTS

| | | | |
|---|---|---|---|
| 3,941,121 | 3/1976 | Olinger et al. | 128/6 |
| 3,982,541 | 9/1976 | L'Esperance | 128/303.1 |
| 4,072,147 | 2/1978 | Hett | 606/3 |
| 4,136,692 | 1/1979 | Goldowsky | 604/251 |
| 4,211,229 | 7/1980 | Wurster | 128/303.1 |
| 4,311,138 | 1/1982 | Sugarman | 604/21 |
| 4,551,129 | 11/1985 | Coleman et al. | 604/21 |
| 4,564,011 | 1/1986 | Goldman | 128/303.1 |
| 4,566,438 | 1/1986 | Liese et al. | 128/6 |
| 4,694,828 | 9/1987 | Eichenbaum | 128/303.1 |
| 4,808,157 | 2/1989 | Coombs | 604/44 |

Primary Examiner—Max Hindenburg
Attorney, Agent, or Firm—Jordan and Hamburg

[57] ABSTRACT

A spinal needle for performing medical treatment is inserted into the vertebral pulp, a laser probe is inserted into the spinal needle, and then laser rays are radiated onto the vertebral pulp. An air-escape tube is unitarily provided parallel to the spinal needle or a flow-passage connected with the interior of the spinal needle is provided in the vicinity of the handle portion of the spinal needle.

15 Claims, 2 Drawing Sheets

SPINAL NEEDLE WITH OPTICAL FIBER MEANS FOR RADIATING A LASER BEAM

BACKGROUND OF THE INVENTION

The present invention relates to a spinal needle, in particular, a spinal needle employed for evaporating the vertebral pulp in the intervertebral disk by utilizing the evaporating action of laser beams with the intention of decreasing the inner pressure of the intervertebral disk.

Hernia of an intervertebral disk occurs with the result that the bone marrow surrounding in the intervertebral disk breaks or possibly destroys the fibrous ring and prolapses into the vertebral canal. One of the methods of treatment, already proposed is that the bone vertebral pulp in the intervertebral disk is evaporated by utilizing the evaporating action of laser rays and thereby the inner pressure of the intervertebral disk is decreased.

In the laser medical treatment according to the prior art technology as mentioned above, at first, the puncturing needle is inserted into the spinal needle, and then the spinal needle is thrust into the intervertebral disk. Next, the puncturing needle is drawn out therefrom. After confirming the position of the spinal needle by use of an X ray apparatus, the laser probe is inserted into the spinal needle and laser rays are radiated on the vertebral pulp in order to evaporate said vertebral pulp. At this time, gas is generated when the vertebral pulp is evaporated, and therefore it is necessary to draw the generated gas out of the human body.

SUMMARY OF THE INVENTION

It is an object of the present invention to provide a spinal needle capable of effectively drawing out the gas which is generated when the vertebral pulp is evaporated by radiating thereon laser rays.

It is another object of the present invention to provide as spinal needle capable of thrusting easily and decreasing the extent of damage to the skin of the human body.

DESCRIPTION OF THE PREFERRED EMBODIMENTS

Figure 1:
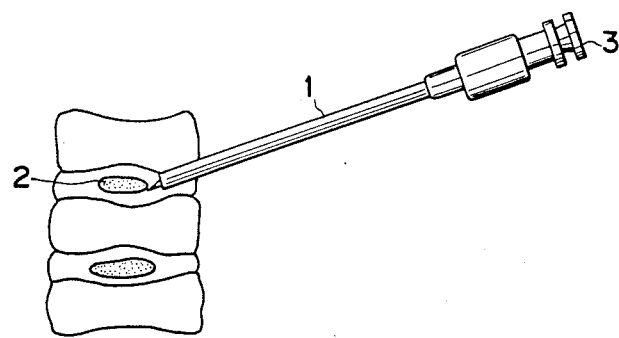
FIGS. 1 through 3 are views for explaining the performing of medical treatment to the vertebral pulp by means of laser beams according to prior art technology.
Figure 2:
Figure 3:
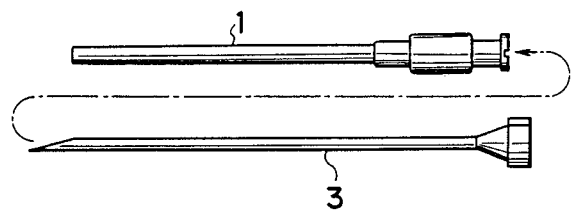

FIGS. 1 through 3 are views for explaining an example of the laser medical treatment according to the prior art technology as mentioned above. In FIGS. 1 through 3, the reference numeral 1 designates a spinal needle, 2 a vertebral pulp, 3 a puncturing needle, and 4 a laser probe. At first, as shown in FIG. 1, the puncturing needle 3 is inserted into the spinal needle 1, and then the spinal needle 1 is thrust into the intervertebral disk. Next, the puncturing needle 3 is drawn out therefrom. After confirming the position of the spinal needle 1 by use of an X ray apparatus, the laser probe 4 is inserted into the spinal needle 1 and laser rays are radiated on the vertebral pulp 2 in order to evaporate said vertebral pulp. At this time, gas is generated when the vertebral pulp 2 is evaporated, and therefore it is necessary to draw the generated gas out of the human body.

The present invention was made in consideration of the situation as described above. In particular, it is the object of the present invention to provide a spinal needle capable of effectively drawing out the gas which is generated when the vertebral pulp is evaporated by radiating thereon laser rays.

Figure 4:
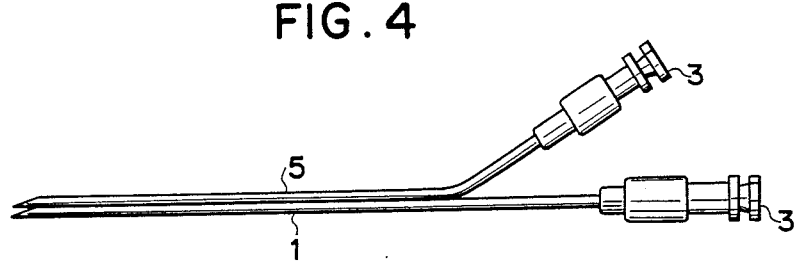
FIG. 4 is an outline view showing an embodiment of a spinal needle having an air-escape tube according to the present invention.

FIG. 4 is a construction view for explaining an embodiment of a spinal needle having an air-escape tube according to the present invention. In FIG. 4, the reference numeral 1 designates a spinal needle exerting such an action on the vertebral, pulp as mentioned above. The numeral 5 designates an air-escape tube. In the present embodiment, the air-escape tube 5 is provided parallel to the spinal needle 1 outside thereof and unitarily combined with the spinal needle 1.

At first, a puncturing needle 3 is inserted, respectively, into the spinal needle 1 and the air-escape tube 5. Then the combined needle assembly is thrust into the vertebral pulp. After thrusting it thereinto, each of the puncturing needles 3 are respectively drawn out of the spinal needle 1 and the air-escape tube 5, and then the laser probe 4 is inserted into the spinal needle 1 in place of the puncturing needle 3 in order to cause the evaporation of the vertebral pulp as mentioned above. In such a construction, when the laser beams are radiated onto the vertebral pulp, the latter is evaporated and the gas generated at the time of the spinal core's evaporation can be effectively drawn out through the air-escape tube 5 into the atmosphere.

Moreover, in the case of plating the inner wall portion of the spinal needle 1 with metal, for instance, with gold or the like, the laser beams radiated into the spinal needle 1 are effectively reflected therein and radiated from the tip end portion thereof. Furthermore, since there is a chance of heating in the spinal needle 1, resulting from the loss of laser rays, etc., it may be preferable to cover the spinal needle 1 with a heat-proof coat of ceramic, silicone, teflon or the like.

However, in the spinal needle shown in FIG. 4, since the spinal needle 1 and the air-escape tube 5 are unitarily formed and the thrusting surface thereof is formed in a complex shape, as for instance, in the cross-section shape of the letter "8", there remains such a problem to be solved that the thrusting surface of the unitarily combined needle assembly may damage the skin of a patient more extensively than is necessary.

Therefore, it is another object of the invention to provide a spinal needle capable of thrusting easily and decreasing the extent of damage to the skin of the human body.

Figure 5:
FIGS. 5(a) and 5(b) are outline views showing another embodiment of the present invention.
Figure 5:
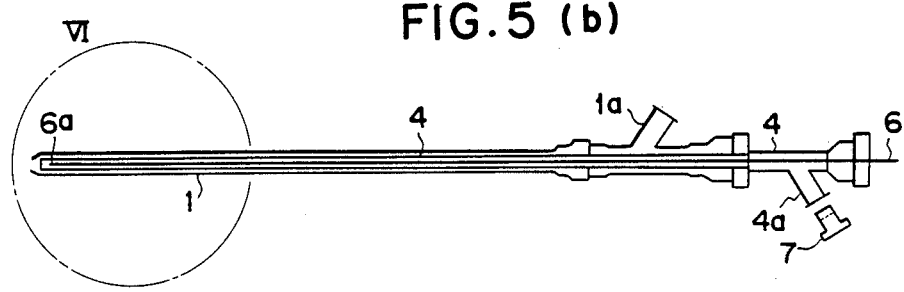

The spinal needle shown in FIGS. 5(a) and 5(b) overcome the defect as mentioned above. This spinal needle is constructed such that the spinal needle itself 1 has the function of drawing out the gas generated therein. FIG. 5(a) shows a condition in which the puncturing needle 3 is inserted into the spinal needle 1 while FIG. 5(b) shows another situation in which puncturing needle 3 is drawn out from the spinal needle 1 and the laser probe 4 is inserted therein instead. An optical fiber 6 for transmitting the laser beams therethrough and radiating laser beams therefrom onto a desired place is inserted into the laser probe 4. The laser light rays are transmitted to the optical fiber 6 through an end portion not shown in FIGS. 5(a) and 5(b) and radiated from its tip end portion 6a onto a desired part of a human body, as for instance the vertebral pulp. In such a way, evaporation of the vertebral pulp is accomplished.

Furthermore, in the present embodiment, a gas drawing-out flow-passage 1a connected with the interior of the spinal needle is unitarily combined with the spinal needle 1 in the vicinity of the handle portion thereof. In such a construction, the laser probe 4 is inserted into the spinal needle 1 in order to evaporate the vertebral pulp as shown in FIG. 5(b). On that occasion, the generated gas is discharged outside of the human body through the gas drawing-out flow-passage 1a after passing through the gap formed between the spinal needle 1 and the laser probe 4.

And further, as shown in FIG. 5(b), when a flow-passage 4a, communicating with the interior of the laser probe 4, is provided in the vicinity of the handle portion of the laser probe 4, it may be possible to introduce, for instance, a physiological salt solution into the interior of the laser probe 4 and draw out such solution outside of the spinal needle assembly through the gas drawing-out flow-passage 1a. In such a way, dirt from the optical fiber 6 can be removed and the interior of the spinal needle 1 can be cleaned.

Furthermore, the gas generated in the interior of the vertebral pulp can be drawn out by sucking the gas through the gas drawing-out flow-passage 1a. At this time, since air flows therein through the flow-passage 4a, the generated gas can be drawn out still more effectively. However, in the case of simply letting atmospheric air flow in through the flow-passage 4a, it turns out to be very unsanitary. On this occasion, it is necessary to install a membrane filter or the like at the flow-in passage 4a in order to prevent various bacteria contained in the atmosphere from entering the vertebral pulp. Namely, in FIG. 5(b), the reference numeral 7 designates a membrane filter. When the gas is sucked out, the spinal needle assembly is employed by installing the filter 7 at the flow-in passage 4a. On the other hand, at the time of flushing, the assembly is used after removing the filter 7 therefrom. And further, it may be possible that the optical fiber 6 is inserted into the laser probe needle 4 so as to be positioned at a predetermined location, or that, after inserting the laser probe needle 4 into a desired place, the optical fiber 6 is inserted into the laser probe needle 4. On this occasion, the length (depth) of its insertion is determined beforehand by use of a stopper or the like.

Figure 6:
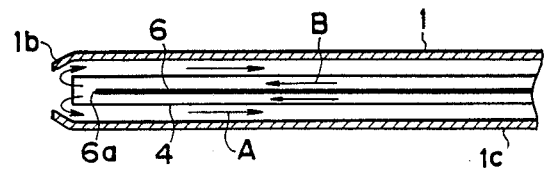
FIG. 6 is a partially enlarged view of the portion VI shown in FIG. 5(b).

FIG. 6 is a partially enlarged view of the portion VI shown in FIG. 5(b). Concerning the relationship of the spinal needle 1, laser probe needle 4 and the optical fiber 6, the tip end of the laser probe needle 4 is adjusted so as to be positioned at the location shown in FIG. 6 on the inner side of the spinal needle 1, and the tip end of the optical fiber 6 is adjusted so as to be positioned also at another location shown in FIG. 6. in the inner side of the laser probe needle 4. In such a way, the drawing-out of the gas can be facilitated. In addition, burn-out damage of the human body's tissues, dirt of the optical fiber's tip end, etc. can be prevented.

Moreover, in FIG. 6, the arrow mark A represents a flow-passage communicating with the flow-passage 1a and the arrow mark B represents another flow-passage communicating with the flow-passage 4a. At the time of flushing, a physiological salt solution flowing in via the flow-passage 4a passes through the flow-passages B and A and flows out through the flow-passage 1a outside of the spinal needle assembly. Furthermore, a tapered portion 1b is provided at the tip of the spinal needle 1. In such a construction, the spinal needle 1 can be thrust easily and decrease the extent of damage to the skin of a human body. Furthermore, the outer circumferential portion of the spinal needle 1 excluding the afore-mentioned tapered portion is coated with a material 1c such as ceramic, silicone, teflon etc. It may also be possible to prevent heat from escaping from the living body's tissues through the spinal needle 1.

I claim:

1. A spinal needle insertable into the vertebral pulp to a treatment site comprising a hollow first cylinder means having an open distal end disposable at said treatment site, a second cylinder means disposed within said first cylinder means, said first cylinder means having an inner diameter greater than the outer diameter of said second cylinder means to thereby define a first flow passage between said first and second cylinder means, optical fiber means disposed within said second cylinder means for radiating a laser beam through said open distal end of said first cylinder means to said treatment site, said second cylinder means having an inner diameter greater than the outer diameter of said optical fiber means to thereby define a second flow passage between said second cylinder means and said optical fiber means, fluid introduction means on said second cylinder means for introducing a fluid into said second flow passage, said second cylinder means having an open distal end terminating within said first cylinder means juxtaposed to said open distal end of said first cylinder means such that said fluid passes from said open distal end of said second cylinder means into said first cylinder means and is evacuated through said first passage means, said open distal end of said first cylinder means receiving gas generated at said treatment site when the vertebral pulp is evaporated by radiating said laser beam onto said treatment site, said generated gas being evacuated through said first flow passage, said distal end of said first cylinder means having a converging section which converges radially inwardly to define a taper to facilitate insertion and penetration of said spinal needle into a person's body to said treatment site.

2. A spinal needle according to claim 1, wherein said distal end of said first cylinder means has a terminating end part, said converging section converging radially inwardly as said terminating end part is approached.

3. A spinal needle according to claim 2, wherein said distal end of said first cylinder means has an outer wall, said outer wall having said converging section.

4. A spinal needle according to claim 1, wherein said distal end of said first cylinder means has converging inner and outer walls which define said converging section.

5. A spinal needle according to claim 1, wherein said distal end of said first cylinder means has a terminating end part, said distal end of said second cylinder means having a terminating end part which is disposed within said first cylinder means to thereby define a space within said first cylinder means between said terminating end parts of said first and second cylinder means such that fluid in said second cylinder means exits said open distal end of said second cylinder means and passes into said space to make a directional turn in said space and then flow into said first flow passage.

6. A spinal needle according to claim 5, wherein said optical fiber means has a distal end having a terminating end part which is disposed within said second cylinder means to thereby define a space within said second cylinder means between said terminating end part of said second cylinder means and said terminating end part of said optical fiber means.

7. A spinal needle according to claim 6, wherein said optical fiber means radiates said laser beam through said open distal ends of said first and second cylinder means.

8. A spinal needle according to claim 1, wherein said open distal end of said first cylinder means defines an end opening for receiving said gas generated at said treatment site, said end opening having a diameter less than the internal diameter of said outer cylinder means such that said converging section defines a constriction at the end of said first cylinder means.

9. A spinal needle according to claim 1, wherein said first cylinder means, said second cylinder means, and said optical fiber means each have a common longitudinal axis.

10. A spinal needle according to claim 1 further comprising evacuating means on said first cylinder means for evacuating fluid from said second flow passage.

11. A spinal needle insertable into the vertebral pulp to a treatment site comprising a hollow first cylinder means having an inner longitudinal end disposable at said treatment site, a second cylinder means disposed within said first cylinder means, said first cylinder means having an inner diameter greater than the outer diameter of said second cylinder means to thereby define a first flow passage between said first and second cylinder means, optical fiber means disposed within said second cylinder means for radiating a laser beam, said second cylinder means having an inner diameter greater than the outer diameter of said optical fiber means to thereby define a second flow passage between said second cylinder means and said optical fiber means, irrigation fluid introduction means on said second cylinder means for introducing an irrigation fluid into said second flow passage such that said irrigation fluid passes from said second flow passage to said first flow passage, said inner longitudinal end of said first cylinder means receiving gas generated at said treatment site when the vertebral pulp is evaporated by radiating said laser beam onto said treatment site, said generated gas being evacuated through said first flow passage, said first cylinder means having an inner wall and an outer wall radially spaced from one another, said inner wall and said outer wall having longitudinal end portions which converge radially inwardly to thereby define a tapered end at said inner longitudinal end of said first cylinder means to facilitate insertion and penetration of said needle into a person's body to said treatment site.

12. A spinal needle according to claim 11, wherein said second cylinder means has an inner longitudinal end which terminates at a position juxtaposed to said tapered end of said first cylinder means such that irrigation fluid in said second flow passage exits from said inner longitudinal end of said second cylinder means to effect irrigation and then flows into said first flow passage for evacuation.

13. A spinal needle according to claim 11, wherein said second cylinder means has an inner longitudinal end which terminates within said first cylinder means such that said first cylinder means is longer than said inner longitudinal end of said second cylinder means.

14. A spinal needle according to claim 13, wherein said optical fiber means has an inner longitudinal end which terminates within said second cylinder means such that said second cylinder means is longer than said inner longitudinal end of said optical fiber means.

15. A spinal needle according to claim 14, wherein said inner longitudinal end of said first cylinder means and said inner longitudinal end of said second cylinder means are open, said inner longitudinal end of said optical fiber means transmitting a laser beam through said open inner longitudinal ends of said first cylinder means and said second cylinder means onto said treatment site.

* * * * *